United States Patent [19]

Taylor

[11] 4,115,902

[45] Sep. 26, 1978

[54] BRACE HINGE

[75] Inventor: Glenn N. Taylor, Cary, Ill.

[73] Assignee: The Kendall Company, Boston, Mass.

[21] Appl. No.: 878,051

[22] Filed: Feb. 15, 1978

Related U.S. Application Data

[62] Division of Ser. No. 792,824, May 2, 1977.

[51] Int. Cl.² ............................................. E05D 15/58
[52] U.S. Cl. .................................. 16/179; 16/DIG. 13; 2/24; 403/364
[58] Field of Search ...................... 16/179, 128 R, 130, 16/141, 144, 150, DIG. 13; 128/80 R, 80 C, 87 R, 89 R, 133, 165; 2/16, 22, 24; 99/379, 402; 109/62; 308/2 A; 403/364

[56] References Cited

U.S. PATENT DOCUMENTS

| 1,101,786 | 6/1914 | Craine | 403/364 |
| 1,359,452 | 11/1920 | Walker | 403/364 X |
| 3,927,438 | 12/1975 | Blake | 16/150 |

FOREIGN PATENT DOCUMENTS

| 1,496,136 | 8/1967 | France | 16/128 R |
| 1,553,553 | 8/1969 | Fed. Rep. of Germany | 16/128 R |

Primary Examiner—Werner H. Schroeder
Assistant Examiner—Moshe I. Cohen
Attorney, Agent, or Firm—Powell L. Sprunger

[57] ABSTRACT

A brace hinge comprising a pair of opposed housings having a plurality of elongated flexible alternate ribs extending from the opposed housings, with the ribs of each housing being slidably received intermediate the ribs of the other housing.

11 Claims, 15 Drawing Figures

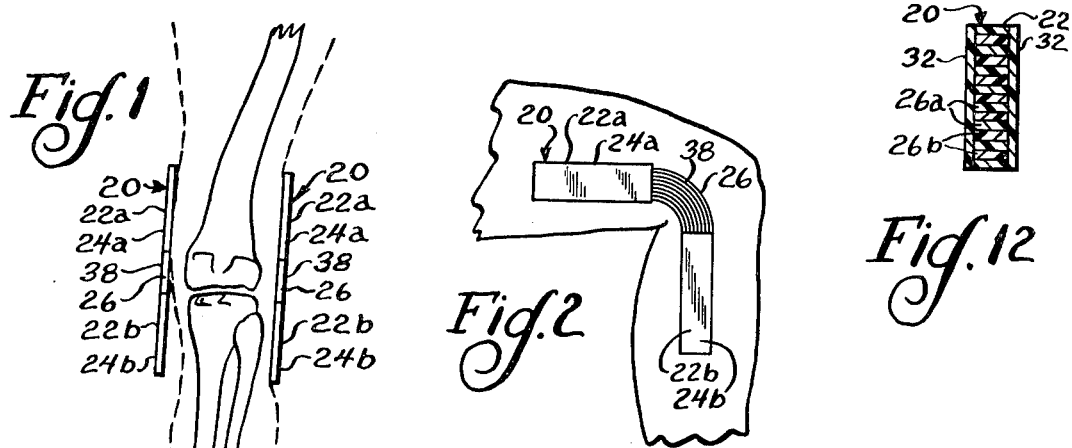
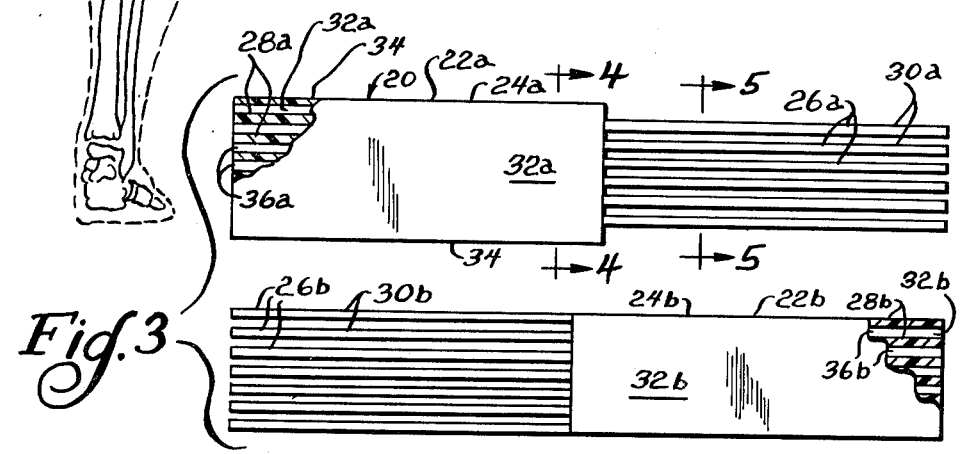
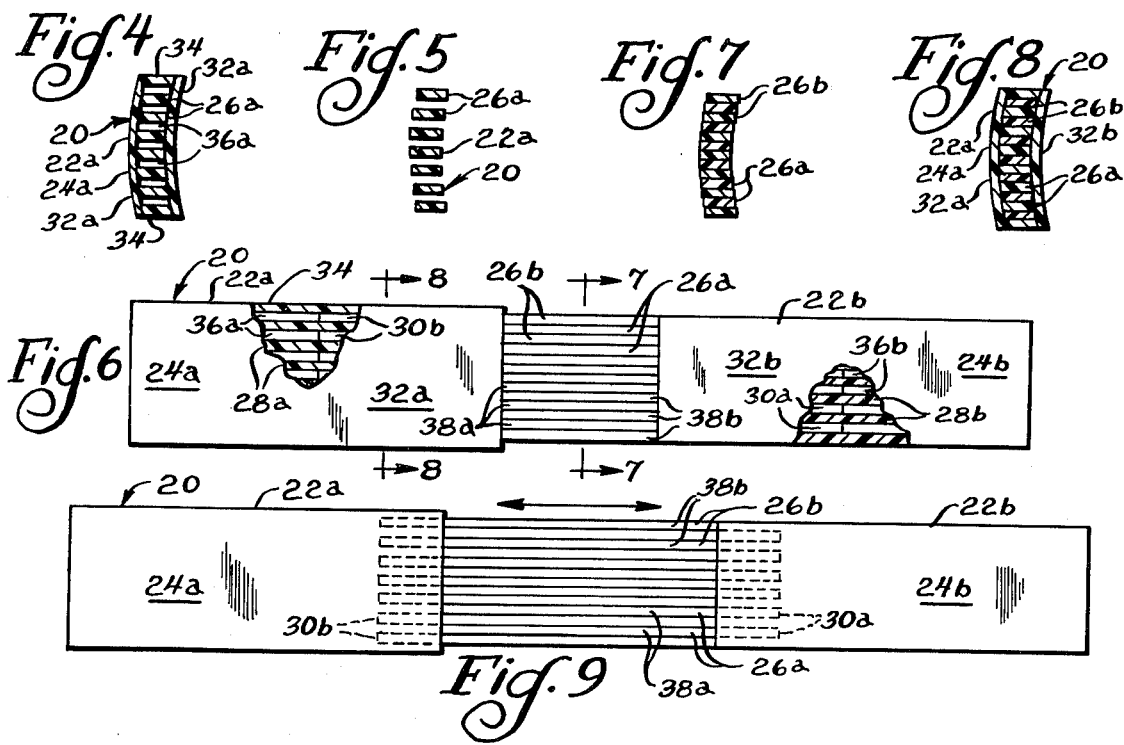

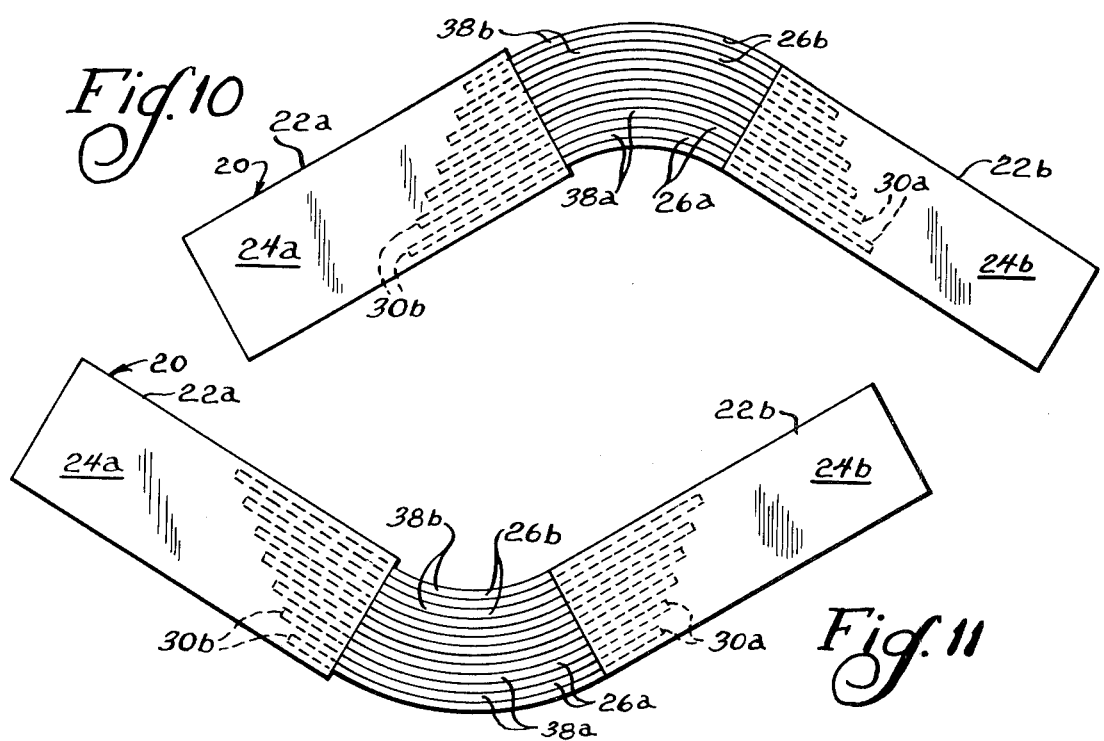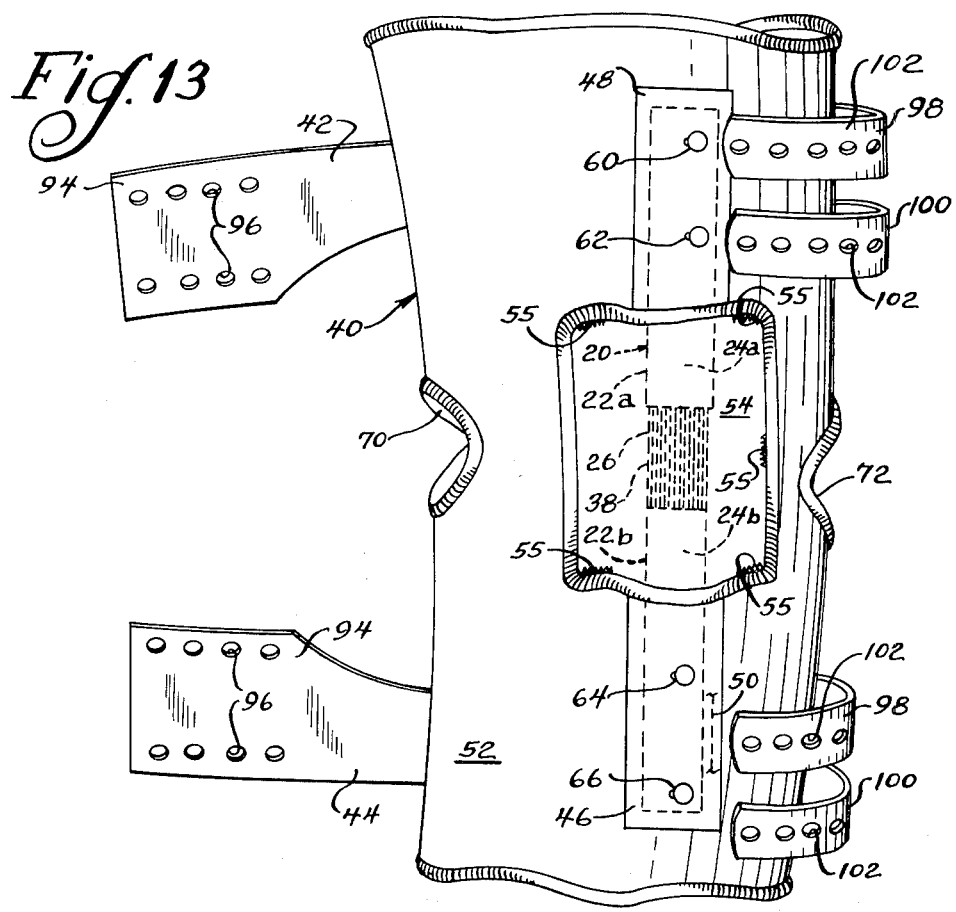

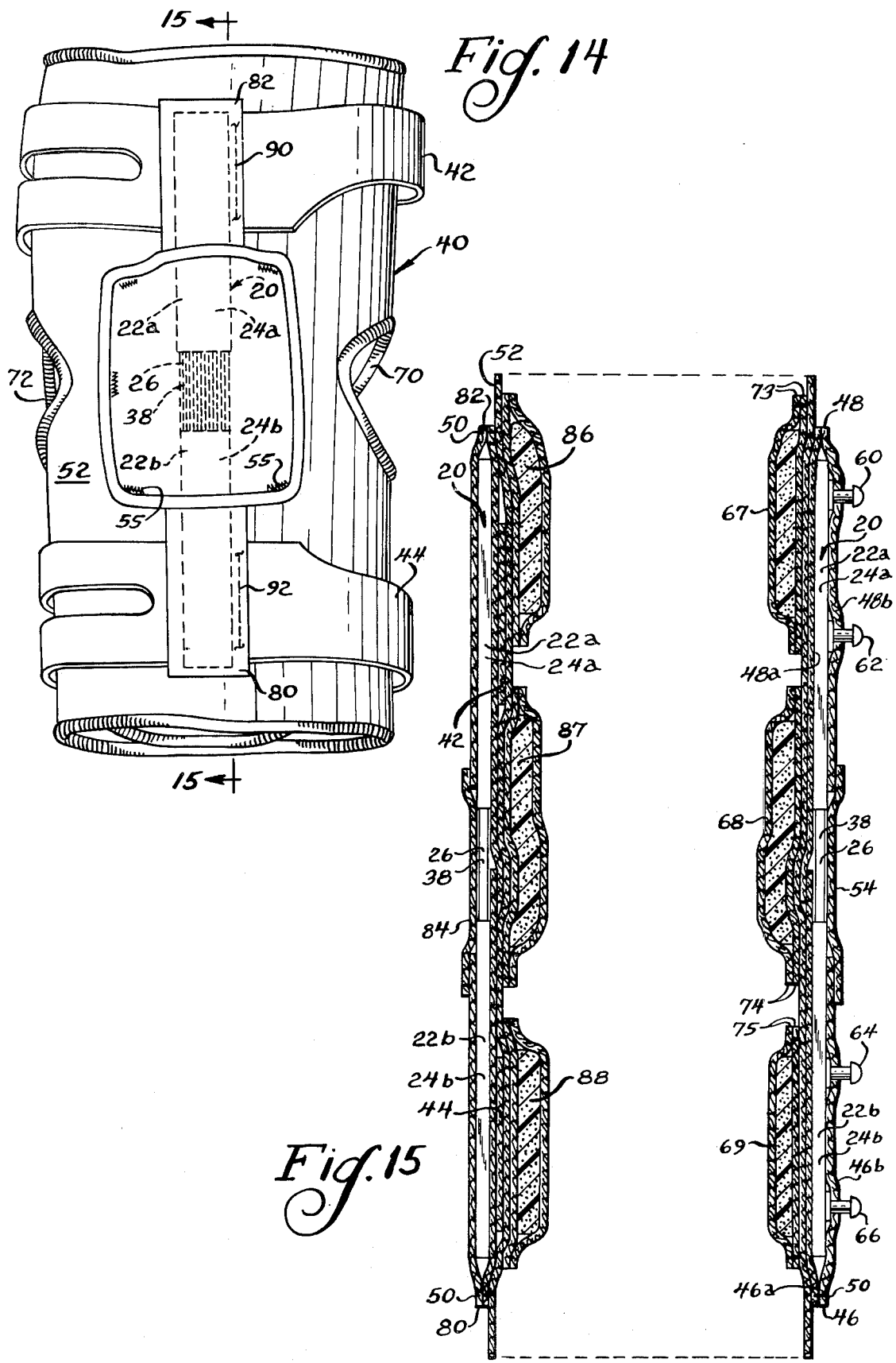

BRACE HINGE

This is a division, of application Ser. No. 792,824 filed May 2, 1977.

SUMMARY OF THE INVENTION

The present invention relates to hinges, and more particularly to brace hinges for a wearer's joint, such as the knee.

Although the knee-joint has been described as a hinge joint, it is more complicated in nature, and may be considered as having three articulations of two different types. The first type of motion is a condyloid articulation and an ovoid articular surface, or condyle, is received in an elliptical cavity to permit flexion, extension, abduction, adduction, and circumduction, without axial rotation of the joint. The second type of articulation is arthrodial which only permits gliding movement. Such motion is defined by the apposition of plane surfaces, or one slightly concave and the other slightly convex, with the amount of motion between the surfaces being limited by the ligaments or osseous processes surrounding the articulation.

The knee-joint is made up of two condyloid joints and a third joint which is partially arthrodial, since the articular surfaces are not mutually adapted to each other and the movement is not a simple gliding one. The principal movements that take place at the knee-joint are flexion and extension. The movements of flexion and extension at this joint differ from those in a typical hinge joint, since the axis around which motion takes place is not fixed but shifts forward during extension and backward during flexion.

Individuals who have sustained knee injuries, who have had operations to remove cartilage, or who have weak knee joints from causes such as arthritis primarily need protection against lateral motion of the knee in a direction transverse to the plane of flexion and extension, such as might be caused by a blow to the side of the knee. At the same time, a suitable knee brace should not interfere with the normal flexion and extension of the leg. The brace should protect the knee against sidewise motions during both flexion and extension, and should lie parallel the leg proximal and distal the knee joint at all positions of the joint.

A various assortment of hinges have been proposed in the past for use in braces, and normally have taken the form of metal structures which in many cases are unduly complex. In addition, the metal hinges result in an undue amount of weight for the brace, and must be removed from the brace itself when it is desired to launder the brace, since the metal hinges may rust. Further, the prior hinges normally have a fixed pivotal structure, and are not normally adjustable in length or in the amount of force required to bend the hinge.

SUMMARY OF THE INVENTION

A principal feature of the present invention is the provision of a brace hinge of simplified construction and improved operation.

The brace hinge of the present invention comprises, a first hinge member having a housing, and a plurality of elongated flexible ribs extending from one end of the housing, with the ribs being spaced laterally across the housing and defining a plurality of laterally spaced grooves extending longitudinally in the housing. The hinge has a second hinge member having a housing, and a plurality of elongated flexible ribs extending from one end of the second member housing, with the second member ribs being spaced laterally across the second member housing and defining a plurality of laterally spaced grooves extending longitudinally in the second member housing. The ribs of the first hinge member are slidably received in the grooves of the second hinge member, and the ribs of the second hinge member are slidably received in the grooves of the first hinge member. A cuff is provided for supporting the hinge adjacent a wearer's joint, such as the knee joint. The cuff has means for securing the housing of one of the hinge members generally parallel the wearer's extremity and proximal the wearer's joint, and means for securing the housing of the other hinge member genenerally parallel the wearer's extremity and distal the wearer's joint.

A feature of the present invention is that the housings of the first and second hinge members are spaced apart in the region of the wearer's joint, such that the rib portions intermediate the housings are located adjacent the joint.

Another feature of the invention is that the rib portions intermediate the housings flex during movement of the wearer's extremity about the joint while end portions of the ribs slide in the housings.

This, a feature of the invention is that the hinge flexes to accommodate motion of the joint.

Still another feature of the invention is that the distance between the housings may be modified.

Thus, a feature of the invention is that the hinge accommodates both normal extension and flexion of the wearer's joint while preventing sidewise motion of the joint whether the extremity is flexed or extended.

Yet another feature of the invention is that the amount of force required to flex the hinge may be modified by adjustment of the distance between the housings.

A further feature of the invention is that the hinge is preferably made from a plastic material, such that the hinge has a relatively light weight and need not be removed from the brace cuff during laundry of the cuff.

Further features will become more fully apparent in the following description of the embodiments of this invention and from the appended claims.

DESCRIPTION OF THE DRAWINGS

In the drawings:

FIG. 1 is a diagrammatic view of a wearer's leg illustrating a pair of hinges of the present invention as positioned on inner and outer sides of the wearer's knee;

FIG. 2 is an elevational view showing the hinge of the present invention as flexed by the wearer's knee;

FIG. 3 is a plan view, partly broken away, illustrating a pair of hinge members for the hinge of the present invention;

FIG. 4 is a sectional view taken substantially as indicated along the line 4—4 of FIG. 3;

FIG. 5 is a sectional view taken substantially as indicated along the line 5—5 of FIG. 3;

FIG. 6 is a plan view, partly broken away, of the hinge of the present invention;

FIG. 7 is a sectional view taken substantially as indicated along the line 7—7 of FIG. 6;

FIG. 8 is a sectional view taken substantially as indicated along the line 8—8 of FIG. 6;

FIG. 9 is a plan view of the hinge of the present invention illustrating adjustment in the length of the hinge;

FIGS. 10 and 11 are plan views illustration flexation of the hinge of the present invention;

FIG. 12 is a sectional view of another embodiment of the hinge of the present invention;

FIG. 13 is an outer perspective view of a knee brace utilizing the hinge of the present invention;

FIG. 14 is an inner perspective view of the brace of FIG. 13; and

FIG. 15 is a sectional view taken substantially as indicated along the line 15—15 of FIG. 14.

DESCRIPTION OF THE PREFERRED EMBODIMENTS

Referring now to FIG. 1, there are shown inner and outer hinges generally designated 20 in position for bracing a wearer's knee. Although the hinge of the present invention will be described primarily for use in connection with a knee brace, it will be understood that the hinge may be utilized for other suitable purposes, such as a brace for a wearer's elbow.

With reference to FIGS. 3-5, the hinge 20 has first and second hinge members 22a and 22b respectively having a housing 24a and 24b and a plurality of elongated flexible ribs or fingers 26a and 26b. As shown, the first set of ribs 26a are spaced laterally across the first hinge member 22a, with one inner end 28a of the first ribs 26a being received in the housing 24a, and with the other end 30a projecting from the housing 24a. The housing 24a of the first hinge member 22a may comprise a pair of opposed side plates 32a and a pair of end plates 34 secured to the side plates 32a at edges of the housing 24a. The one end 28a of the first ribs 26a are secured to the side plates 32a in a laterally spaced relationship inside the housing 24a, such that the first ribs 26a define a plurality of laterally spaced grooves 36a extending longitudinally in the housing 24a. Also, in the particular form shown, the end plates 34 of the first hinge member 22a are spaced from the adjacent side ribs 26a such that they also define longitudinally extending grooves intermediate the plates 34 and the adjacent ribs 26a.

Similarly, the second hinge member 22b has a pair of side plates 32b secured to one inner end 28b of the second ribs 26b while the other outer end 30b of the second ribs 26b project from the second housing 24b. The one end 28b of the second ribs 26b are spaced laterally across the second housing 24b, such that the ribs 26b define a plurality of laterally spaced grooves 36b extending longitudinally in the second housing 24b. In the particular form, as shown, the side ribs 26b may define end plates of the second housing 24b.

The width of the first ribs 26a is approximately equal to the width of the second ribs 26b, such that the width of the first grooves 36a in the housing 24a is approximately equal to the width of the second ribs 26b, and the width of the grooves 36b in the second housing 24b is approximately equal to the width of the first ribs 26a. Also, the first ribs 26a are spaced apart a distance approximately equal to the thickness of the second ribs 26b, and the second ribs 26b are spaced apart a distance approximately equal to the thickness of the first ribs 26a. Accordingly, the distance or thickness of the first grooves 36a between the first ribs 26a is approximately equal to the thickness of the second ribs 26b, and the distance or thickness of the second grooves 36b between the second ribs 26b is approximately equal to the thickness of the first ribs 26a.

The first and second hinge members 22a and b are assembled into the hinge 20, as illustrated in FIGS. 6-8. As shown, the ribs 26a of the first hinge member 22a are received in the grooves 36b of the second hinge member 22b intermediate the second ribs 26b, and the ribs 26b of the second hinge member 22b are received in the grooves 36a of the first hinge member 22a intermediate the first ribs 26a. Thus, in this configuration, the outer ends 30a of the first ribs 26a are received in the housing 24b of the second hinge member 22b, while the outer ends 30b of the second ribs 26b are received in the housing 24a of the first hinge member 22a. Due to the relative spacing between the ribs 26a and b of the housings 24a and b, it will be apparent that the ribs 26a of the first hinge member 22a are slidably received in the grooves 36b of the second hinge member 22b, and the ribs 26b of the second hinge member 22b are slidably received in the grooves 36a of the first hinge member 22a, with the contiguous ribs 26a and b being closely spaced and generally parallel in a relaxed condition of the hinge 20. With reference to FIGS. 6 and 9, the spacing or distance between the housings 24a and b may be suitably adjusted through movement of the housings 24a and b relative each other while the ribs 26a and b slide in the associated grooves 36b and a. As shown, when the housings 24a and b of the first and second hinge members 22a and b are spaced apart, portions 38a and 38b of the respective alternate ribs 26a and b are located intermediate the housings 24a and b.

With reference to FIGS. 6-8, in one form, the hinge members 22a and b may be slightly curved laterally across the hinge members 22a and b in order to conform to the contour of the wearer's extremity. In an alternative form, as shown in FIG. 12, the hinge may be formed in a generally planar configuration laterally across the hinge member 22.

The ribs 26a and b may be made of any suitable flexible material. However, in a preferred form, the ribs 26a and b are made of a suitable plastic material, such as polycarbonate, in order to reduce the weight of the hinge 20 and permit convenient laundering of a brace in which the hinge 20 is placed without concern of damage to the hinge 20 which otherwise might be caused to a metal hinge due to rust. Thus, the side plates 32a and b and end plates 34 may also be made of a suitable plastic material in order to accomplish this result.

With reference to FIGS. 10 and 11, in a spaced configuration of the housings 24a and b, the intermediate portions 38a and b of the ribs 26a and b are permitted to flex while the outer ends 30a and b of the ribs 26a and b slide in the grooves of the housings 24b and a, respectively, in which they are received. Thus, the ribs 26a and b permit relative movement of the housings 24a and b during flexation of the ribs 26a and b. In addition, it will be apparent that the amount of force required to flex the ribs 26a and b in the hinge 20 will be dependent upon the spacing between the housings 24a and b, such that the required force may be modified by suitable adjustment of the distance between the housings 24a and b. Further, the spacing between the housings 24a and b may be adjusted for a particular brace in which it will be placed and for the particular requirements of a wearer's joint.

With reference to FIGS. 1 and 2, inner and outer hinges 20 may be secured on opposed sides of the wearer's joint, such as the knee, as shown, with the housings 24a of the first hinge members 22a being secured on opposed sides of the wearer's extremity proximal the joint, and with the housings 24b of the second hinge members 22b being secured on opposed sides of the wearer's extremity distal the joint. In addition, the housings 24a and b of the hinges 20 are spaced apart, such that the intermediate portions 38 of the hinge ribs are located adjacent the joint. In this configuration, the hinges permit extension of the joint, since the housings 24a and b are permitted to move relative each other in a longitudinal direction while the ribs of the hinge members 22a and b slide in the associated grooves. Further, with reference to FIG. 2, the hinges permit flexation of the joint during flexation of the rib portions 38, with the housings 24a and b of the hinges 20 remaining at relatively fixed longitudinal positions proximal and distal the wearer's joint. As previously indicated, the amount of force required to flex the hinge may be adjusted through modification of the spacing between the housings 24a and b of the first and second hinge members 22a and b. When secured in place along the sides of the wearer's joint, the hinges 20 thus support the wearer's joint while permitting extension and flexation of the joint.

With reference to FIGS. 13–15, the inner and outer hinges 20 are retained in a harness of a knee brace 40. The harness has an upper strap 42 and a lower strap 44 immovably secured with respect to the inner hinge, and attachable to the outer hinge. The harness also has an elastic cuff 52 and internal padding for the comfort of the wearer.

With respect to the outer hinge, the proximal or first housing 24a of the hinge member 22a is retained in a leather pocket 48 having an inner layer 48a and an outer layer 48b. The distal or second housing 24b of the second hinge member 22b is retained in a leather pocket 46 having an inner layer 46a and an outer layer 46b. The pockets 46 and 48 are secured to the elastic cuff 52 by suitable means, such as by lines of stitching 50. The cuff 52 may be made of any suitable material, such as a two-way stretch fabric. The outer layers 48b and 46b of the pockets are spaced from the intermediate portions 38 of the ribs 26. The cuff 52 may have an outer cover 54 of elastic material secured by stitching 55 to the cuff 52 in order to cover the intermediate portions 38 of the ribs 26. However, the cover 54 is sufficiently free from the cuff 52 to permit flexation of the ribs 26 beneath the cover 54. The inner layers 48a and 46a of the pockets 48 and 46 may overlap beneath the intermediate portions 38 of the ribs 26.

The cuff 52 preferably has a central back opening 70 to prevent binding of the cuff material when the knee is flexed, and a central front opening 72 to assist the wearer in centering the harness over the knee cap. The cuff 52 has a pair of proximal posts 60 and 62 extending through the outer layer 48b of the pocket 48, such that the posts 60 and 62 are retained at a fixed position relative the proximal housing 24a of the outer hinge. Similarly, the cuff 52 has a pair of distal posts 64 and 66 which are secured at a fixed position relative the distal housing 24b of the outer hinge. The cuff 52 also has internal pads 67, 68, and 69 of a suitable material, such as foam, having elastic covers 73, 74, and 75, respectively located adjacent the proximal housing 24a, the intermediate rib portions 38, and the distal housing 24b.

The inner hinge 20 is similarly retained in the cuff 52. Thus, the cuff 52 has a pair of leather pockets 80 and 82 to receive the distal and proximal hinge housings 24b and a, respectively, an outer elastic cover 84 to cover the intermediate rib portions 38, and inner foam pads 86, 87, and 88. As shown, the upper strap 42 passes between the upper pocket 82 and the cuff 52, and the pocket 82 and strap 42 are secured to the cuff 52 by suitable means, such as by a line of stitching 90. Thus, the strap 42 is retained at a fixed position relative the proximal housing 24a of the inner hinge. Similarly, the lower strap 44 is retained at a fixed position by stitching 92 relative the distal housing 24b of the inner hinge, with the strap 44 passing between the lower inner pocket 80 and the cuff 52.

Accordingly, the proximal and distal housings 24a and b of the inner and outer hinges 20 are retained in the leather pockets of the harness in order to prevent angular movement of the hinges 20 relative the wearer's extremity. However, the housings 24a and b of the inner and outer hinges are permitted to longitudinally move slightly within the pockets in order to provide additional flexibility in following the action of the wearer's knee.

As shown, the upper and lower straps 42 and 44 include a back strap portion 94 having two rows of openings 96, and a pair of front strap portions 98 and 100 with each having a row of openings 102. After placement of the knee brace 40 about the wearer's extremity, the front opening 72 is centered over the wearer's knee cap. Next, the back strap portions 94 of the straps 42 and 44 are passed around the outer hinge and are secured in place by passing the posts 60, 62, 64, and 66 through the openings 96 of the straps 42 and 44 according to the desired fit of the brace. Next, the front strap portions 98 and 100 of the straps 42 and 44 are passed around the cuff 52 and are secured to the posts 60, 62, 64, and 66 through the openings 102. In this configuration, the bifurcated front strap portions 98 and 100 permit conformation of the straps to the shape of the wearer's extremity. Although the brace 40 has been described as utilizing cooperating posts and strap openings, it will be apparent that any suitable fastening means may be utilized for the straps and cuff, such as hook and loop fastening strips.

The foregoing detailed description is given for clearness of understanding only, and no unnecessary limitations should be understood therefrom, as modifications will be obvious to those skilled in the art.

I claim:

1. A hinge, comprising:
   a first hinge member having a housing, and a plurality of elongated flexible ribs extending from one end of said housing, said ribs being spaced laterally across the housing and defining a plurality of laterally spaced grooves extending longitudinally in the housing; and
   a second hinge member having a housing, and a plurality of elongated flexible ribs extending from one end of the second member housing, the second member ribs being spaced laterally across the second member housing and defining a plurality of laterally spaced grooves extending longitudinally in the second member housing, said ribs of the first hinge member being slidably received in the grooves of the second hinge member, and said ribs of the second hinge member being slidably received in the grooves of the first hinge member.

2. The hinge of claim 1 wherein the width of the grooves in said first and second member housings is approximately equal to the width of the ribs received in said grooves.

3. The hinge of claim 1 wherein the width of the first member grooves is approximately equal to the width of the second member grooves.

4. The hinge of claim 1 wherein the thickness of the grooves in said first and second members is approximately equal to the thickness of the ribs received in said grooves.

5. The hinge of claim 1 wherein the width and thickness of the first member ribs is approximately equal to the width and thickness of the second member ribs.

6. The hinge of claim 1 wherein said ribs of the first and second hinge members are generally parallel in a relaxed condition of the hinge.

7. The hinge of claim 1 wherein the distance between said first and second hinge members is adjustable.

8. The hinge of claim 1 wherein said ribs of the first and second hinge members are made from a plastic material.

9. The hinge of claim 1 wherein the first and second hinge members are slightly curved laterally across the hinge.

10. A hinge, comprising:
a first housing;
a second housing;
a plurality of contiguous elongated ribs of flexible material, with alternate ribs having one end secured in the first housing and the other end received in the second housing, and the remaining ribs having one end secured in the second housing and the other end extending into the first housing.

11. A hinge comprising, first and second opposed housings having a plurality of elongated flexible alternate ribs extending from said opposed housings, with the ribs of each housing being slidably received intermediate the ribs of the other housing.

* * * * *